US006067342A

United States Patent [19]
Gordon

[11] Patent Number: 6,067,342
[45] Date of Patent: May 23, 2000

[54] DIGITAL FILMLESS X-RAY PROJECTION IMAGING SYSTEM AND METHOD

[75] Inventor: Bernard M. Gordon, Manchester-by-the-Sea, Mass.

[73] Assignee: Analogic Corporation, Peabody, Mass.

[21] Appl. No.: 09/074,184

[22] Filed: May 7, 1998

Related U.S. Application Data

[60] Provisional application No. 60/063,567, Oct. 30, 1997.

[51] Int. Cl.⁷ ........................................................ A61B 6/03
[52] U.S. Cl. ................................. 378/19; 378/15; 378/901
[58] Field of Search ................................... 378/4, 15, 19, 378/901, 62, 98.3, 189

[56] References Cited

U.S. PATENT DOCUMENTS

| | | | |
|---|---|---|---|
| 3,708,673 | 1/1973 | Blacker, Jr. | 250/213 |
| 4,029,963 | 6/1977 | Alvarez et al. | 250/360 |
| 4,135,247 | 1/1979 | Gordon et al. | 364/414 |
| 4,398,302 | 8/1983 | Pfeiler | 378/146 |
| 4,417,354 | 11/1983 | Pfeiler | 378/19 |
| 4,527,060 | 7/1985 | Suzuki et al. | 250/327.2 |
| 5,079,426 | 1/1992 | Antonuk et al. | 250/370.09 |
| 5,132,998 | 7/1992 | Tsutsui et al. | 378/99 |
| 5,199,054 | 3/1993 | Adams et al. | 378/21 |
| 5,661,774 | 8/1997 | Gordon et al. | 378/101 |

OTHER PUBLICATIONS

Boone et al., Filter Wheel Equalization In DSA: Simulation Results, Med. Phys. 20(2), Mar./Apr. 1993, pp. 439–448.

Alvarez et al., Energy–Selective Reconstructions in X–ray Computed Tomography, Phys. Med. Biol. 21(5), Feb. 1976, 733–744.

Sabol et al., Practical Application Of A Scan–Rotate Equalization Geometry To Mammography, Med. Phys. 23 (12), Dec. 1996, p. 1987–1996.

Sabol et al., Analytical Description Of The High And Low Contrast Behavior Of A Scan–Rotate Geometry For Equalization Mammography, Med. Phys. 23 (6), Jun. 1996, pp. 887–898.

Sabol et al., Rotary Sanning Equalization Radiography: An Efficient Geometry for Equalization Mammography, Med. Phys. 21 (10), Oct. 1994, pp. 1523–1533.

*Primary Examiner*—David V. Bruce
*Attorney, Agent, or Firm*—McDermott, Will & Emery

[57] ABSTRACT

A system for and method of producing digital filmless X-ray projection images having resolution and dynamic range characteristics comparable to extant photographic film-based images includes an X-ray source directing an X-ray beam through an object to be viewed toward a detector array, a drive mechanism for rotating the detector array in a plane substantially normal to the X-ray beam, and a reconstruction computer for generating an image from projection data taken from the detector array. The system generates a projection data set corresponding to each of a plurality of incremental angular positions of the detector array, and the reconstruction computer combines the data sets to form a two dimensional projection image of the object being viewed.

66 Claims, 6 Drawing Sheets

DIGITAL FILMLESS X-RAY PROJECTION IMAGING SYSTEM AND METHOD

CROSS-REFERENCE TO RELATED APPLICATIONS

This application is based upon provisional application, U.S. Ser. No. 60/063,567 filed Oct. 30, 1997.

STATEMENT REGARDING FEDERALLY SPONSORED RESEARCH

Not Applicable

REFERENCE TO MICROFICHE APPENDIX

Not Applicable

FIELD OF THE INVENTION

The present invention relates generally to computed radiology and to filmless X-ray imaging systems and methods, and more particularly to digital filmless X-ray projection imaging systems and methods having resolution and dynamic range characteristics comparable to or greater than extant photographic film-based imaging systems.

BACKGROUND OF THE INVENTION

In conventional X-ray imaging systems, the object to be imaged (typically a patient) is placed between an X-ray source and a plate of photographic film. The interaction between the patient and the X-ray radiation is captured and stored on the film. The film may then be viewed for diagnostic purposes via an apparatus which back-lights the film. Although diagnostic images on film have good resolution and contrast characteristics, there are significant disadvantages to using such media for storing images. First, physical examinations call for a predetermined level of X-ray energy depending upon which part of the body is being X-rayed, i.e., a peak voltage and maximum milliampere level for powering the X-ray source, and in the case of a pulsed X-ray source, the time duration of each pulse driving the pulsed X-ray source. If the parameters of the X-ray exposure are wrong the resulting X-ray image recorded on film tends to be either under or over exposed, because of the mismatch between the X-ray flux and the film dynamic range, resulting in poor diagnostic quality images.

In the U.S. the estimate of X-ray images recorded on film that are so poor as to require the retaking of the image ("recall") is estimated to be around 20%. Radiologists expect this number to go up, because of greater reliance on X-ray technicians who are typically less trained and often less skillful than the average radiologist.

Digital X-ray images, in contrast to conventional analog images stored on film, can be archived and stored in picture, archive, communication systems (PACS). The use of PACS facilitates transmission of images via networks and modems to support remote diagnosis. The data is therefore easily stored in memory and archived, and more readily transferred than information contained in X-ray film, without deterioration of data. Thus, various digital processing algorithms and techniques become available making it easier to process the data, such as spatial filtering and other image enhancement techniques and transfer the data from one location to another, by network or modem, for example.

In recent years techniques have been developed to overcome these disadvantages of X-ray film. A number of extant methods and associated technologies have been developed, some designed to provide digitized systems, eliminate film, or otherwise improve on the use of film. The following is a summary of the strengths and weaknesses of the major technologies in use today.

Radiographic Equalization: Radiographic equalization is a process in which the entrance X-ray exposure to a patient is increased locally in areas of high attenuation and decreased over areas of low attenuation so as to provide a more homogeneous distribution of X-ray exposure to the recording medium. Radiographic equalization techniques include scanning equalization radiography, scanning slit equalization radiography, digital beam attenuation, light equalization radiography, and rotary-scanning equalization radiography. The latter includes the steps of scanning an object with an x-ray fan beam by traversing the object with the fan beam at each of a plurality of scan angles as defined by the plane of the fan beam. Examples of the latter are described in:

- Sabol et al., "Practical Application of a Scan-Rotate Equalization Geometry to Mammography," *Medical Physics*, 23(12), December 1996.
- Sabol et al., "Analytical Description of the High and Low Contrast Behavior of a Scan-rotate Geometry for Equalization Mammography," *Medical Physics*, 23(6), June 1996.
- Sabol et al., "Rotary Scanning Equalization Radiography: an Efficient Geometry for Equalization Mammography," *Medical Physics*, 21(10), October 1994.
- Boone et al., "Filter Wheel Equalization in DSA: Simulation Results," *Medical Physics*, 20(2), March/April 1993.

Rotary scanning equalization radiography is analogous to first generation computed tomography, as described Sabol et al., "Analytical Description of the High and Low Contrast Behavior of a Scan-rotate Geometry for Equalization Mammography," *Medical Physics*, 23(6), June 1996.

Film Digitizers: The output of a conventional imaging system (i.e., film) may be digitized with a scanning device, so that the costs associated with the storage and retrieval of film are eliminated. The disadvantages of this method are that the use and associated cost of film, along with the disadvantages noted above, have not been eliminated; a relatively high cost, high quality scanning device must be procured and maintained; and additional labor costs are incurred to digitize the films. An exemplary medium resolution scanning device is the ScanJet 6100C, manufactured by Hewlett Packard of Palo Alto, Calif. The ScanJet 6100C has a specified resolution of 600 dpi with up to 2400 dpi of enhanced resolution. An exemplary high resolution scanning device is the Scanmate 5000, manufactured by ScanView Incorporated of Foster City, Calif. The Scanmate 5000 has a specified resolution of 5000 dpi.

Photo Stimulated Luminescence (PSL): The film/screen combination used in a conventional X-ray system may be replaced with a plate that stores X-ray flux. The stored flux is read out at a later time by stimulating the material with a laser and measuring emitted light. Digital images are formed by rectilinearly scanning individualized pixelated areas of the plates and digitizing the emitted light. An advantage of this system is that film is completely eliminated. Another advantage is that the signals representative of pixels of a latent image on a plate can be digitized over a sufficiently large dynamic range so that one should not have to retake the X-ray image. In addition, at least with certain substrate materials, the X-ray dosage can be reduced because the material used has a higher detection quantum efficiency (DQE) than that of standard X-ray film. Thus, even if recalls are required, the amount of X-ray exposure experienced by the patient is comparatively reduced. In addition, the substrate is typically erasable and reusable, while X-ray film is not.

The current disadvantage of this PSL system is the cost of the read out system and the labor costs incurred to process the storage material. An exemplary PSL system and method is described in U.S. Pat. No. 4,527,060, entitled RADIATION IMAGE READ-OUT METHOD AND APPARATUS, invented by Ishikawa et al., assigned to Fuji Photo Film Company, Ltd., of Japan. Fuji Photo Film Company is one of the major suppliers of PSL systems.

Image Intensifier Tubes (IIT). The film/screen combination used in a conventional X-ray system may be replaced with an IIT. An IIT comprises four primary components: a photo cathode, a microchannel plate, a screen and a housing which holds the other components stationary relative to one another. As X-ray photons which have propagated through a patient strike the photo cathode (essentially a flourescent screen), electrons are emitted into the interior of the tube. The electrons are accelerated to produce a small image on a microchannel plate, which is a second fluorescent screen. The image on the second screen is captured using a video camera with a digital output, such as a CCD camera. The resulting system receives an X-ray beam and produces a direct digital output. However, the spatial resolution and dynamic range of an IIT based system are typically less than conventional film. IIT-based systems are commonly found in cardiac scanners. An exemplary IIT is described in U.S. Pat. No. 3,708,673, entitled IMAGE INTENSIFIER TUBE, invented by Blacker et al., and assigned to The Machlett Laboratories, Inc., of Springdale, Conn.

Semiconductor Detectors: The film/screen combination used in a conventional X-ray system may be replaced with a two dimensional array of semiconductors. X-ray photons which have propagated through a patient are either directly detected in the semiconductors or are indirectly detected by placing a scintillating material on top of the array. In the former case, the semiconductor reacts directly to the X-ray energy. In the latter case, the scintillating material converts the X-ray energy into light which is within the detection range of the semiconductor, and the semiconductor reacts to the light. Each element in the array detects X-rays in an area which is approximately 100-microns by 100 microns. The energy detected by each element of the array is digitized and then saved as a pixel in a final digital image. To replace film in general radiographic practice, the array needs to have on the order of 2000 by 2000 elements. The advantage of this system is that film is completely eliminated. The disadvantage of this system is the cost of the detectors and their associated electronics. An exemplary semiconductor detector array is described in U.S. Pat. No. 5,079,426, entitled MULTI-ELEMENT-AMORPHOUS-SILICON-DETECTOR-ARRAY FOR REAL-TIME IMAGING AND DOSIMETRY OF MEGAVOLTAGE PHOTONS AND DIAGNOSTIC X RAYS, invented by Antonuk et al., assigned to The Regents of the University of Michigan.

Outside of cost, the digital X-ray imaging systems employing semiconductor detectors currently are the best for film replacement. Their dynamic range and spatial resolution are comparable to, if not better than, conventional film, unlike IIT systems. Furthermore, the output of the detector can be fed directly into a PACS, unlike systems using PSL and film digitizers. There is thus a need for a less costly digital X-ray imaging system having spatial resolution and dynamic range sufficient for medical diagnoses.

It is an object of the present invention to substantially overcome the above-identified drawbacks of the prior art.

It is a further object of this invention to provide an X-ray detection system to replace conventional photographic film imaging systems.

It is another object of this invention to provide an X-ray detection system which provides a direct digital output.

It is a further object of this invention to provide an X-ray detection system which provides a direct digital output having a spatial resolution and dynamic range sufficient for medical diagnoses.

SUMMARY OF THE INVENTION

The present invention is directed to an X-ray imaging system that generates digital projection images. In accordance with one aspect of the invention the X-ray imaging system comprises a source of X-ray radiation which produces an X-ray beam along a transmission axis, a detection assembly including a plurality of detectors which receive the X-ray beam, and a rotating mechanism, attached to the detector assembly, for rotating the detectors about the transmission axis (so that the rotation axis and transmission axis are preferably coaxial with one another). As the detectors rotate about the transmission axis, the system generates a set of projection data at each of a plurality of incremental angular positions. An image of an object disposed within the transmission beam between the source and the detectors can be reconstructed from the sets of projection data.

In accordance with another aspect of the invention the X-ray imaging system preferably utilizes a one dimensional (1D) array of detectors (i.e., preferably one row of detectors), thus significantly reducing the total number of detectors necessary to produce an image, and yet providing a similar spatial resolution offered by the (2D) systems (using square matrices of pixelated areas) of the prior art. Thus, by properly selecting the detection medium and providing a sufficient number and density of detectors, one can produce an image having the spatial resolution and dynamic range as provided by the prior art systems at a significantly reduced cost.

In accordance with another embodiment, the detector array is arrange in two rows offset from one another to increase the amount of spatial projection data for providing even better quality images.

In one specific embodiment of the invention, the detectors of a 1D array are arranged in a row, with the transmission axis passing through one of the detectors an equal distance from the two edges defining the width of the detector so as to provide a centered or "one-half" of a detector width arrangement. The detector array need only rotate 180° to provide a sufficient number of sets of projection data for reconstructing an image since the data is duplicated with a second 180° rotation.

In accordance with another specific embodiment the transmission axis passes through one of the detectors three-quarters from one edge of the detector, and one-quarter from the opposite edge of the detector so as to define a "one-quarter" of a detector width offset. The projections acquired at each incremental angle during the first 180° of rotation will then be spatially interleaved with the projections acquired at a corresponding incremental angle during the second 180° of rotation. This provides twice the amount of spatial data with one 360° rotation of the detector array than provided with the one-half detector width arrangement.

In accordance with another specific embodiment, the detectors can be arranged in two rows offset from one another, one row being positioned relative to the transmission axis by a "one-eighth" of a detector width offset, and one row being positioned relative to the transmission axis by "three-eighths" of a detector width offset so as to provide four times the amount of spatial data with one 360° rotation of the detector array than provided with the one-half detector width arrangement.

In accordance with one embodiment of the invention, the detectors are disposed in a plane substantially normal to the transmission (rotation) axis. In another embodiment the detectors are disposed along a curved surface, e.g., a cylindrical surface having an axis of curvature passing through the focal spot of the X-ray beam so that the path length from the source to each detector is substantially the same.

In accordance with one embodiment the detectors convert the X-ray radiation into digital data for processing by a digital computer system so that an image can be reconstructed.

In another embodiment the detectors are formed so as to provide individual detection areas, and can be separate elements. Each of the detectors includes an X-ray converter comprising, for example, a scintillating material (such as a crystal) which converts X-ray radiation into light, and a transducer (such as a photoconductive diode) which converts the light emitted from the corresponding scintillating material into an electrical signal. Alternatively, each detector can be a semiconductor device. The resulting electrical signal is representative of some characteristic of the X-ray radiation received by the scintillating material, such as frequency, energy level or amplitude.

In another embodiment, a light transmissive device, such as a light pipe, can be used to couple the output of each X-ray converter to the corresponding detector.

In another embodiment, a substantially X-ray opaque mask with an X-ray translucent aperture pattern is inserted in the beam path between the X-ray radiation source and the detectors, so as to window the X-ray beam prior to the beam reaching the detectors. In a first embodiment the aperture pattern is circular, and in another embodiment the aperture pattern is star shaped.

In another embodiment, each of the detectors includes a collimator for isolating a portion of the X-ray beam and directing that portion of the beam to the detector.

In another embodiment, an acquisition system samples the detectors at substantially equal angular incremental positions over a range of rotation so as to produce a plurality of projection data sets, each of which corresponds to X-ray radiation received by the detectors at a corresponding one of the angular positions, and a reconstruction computer processes the projection data sets so as to produce an image representative of an object through which the X-ray radiation propagates.

In a further embodiment, at least for some applications the source of X-ray radiation alternates between at least a first energy level and a second energy level, and the image reconstruction computerized system uses projection data corresponding to the two energy levels to generate images corresponding to unique characteristics of the object being viewed.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE INVENTION

Figure 1:
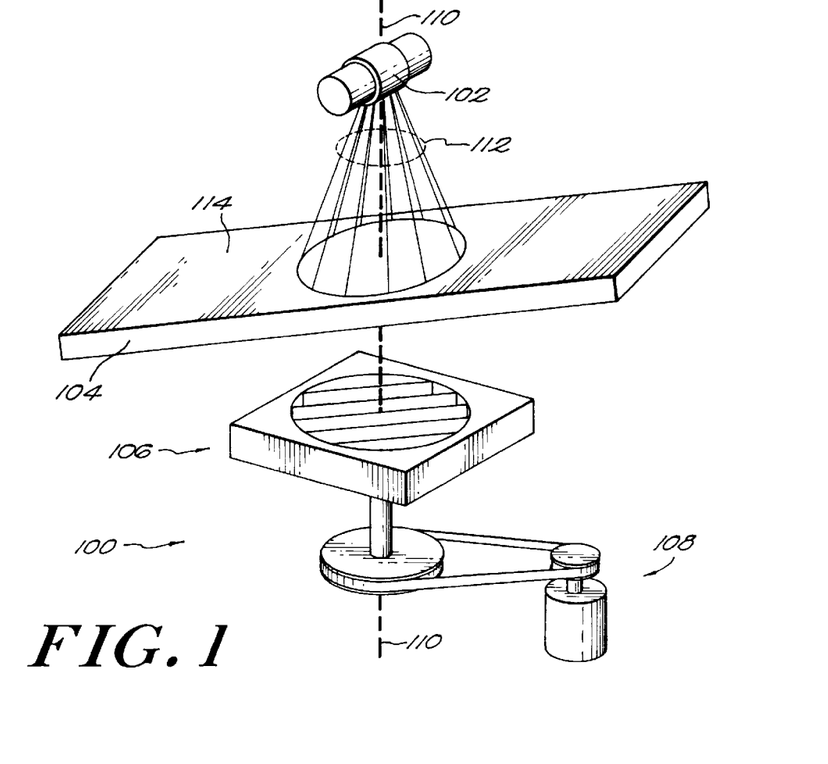
FIG. 1 shows, in perspective view, one embodiment of an X-ray imaging system.

The present invention is directed to a digital filmless X-ray projection imaging system. An exemplary embodiment of an X-ray imaging system is shown in FIG. 1 at 100. The imaging system 100 generally comprises an X-ray source 102, a radio-translucent table 104, a rotatable detector assembly 106 and a drive mechanism 108 for rotating the assembly 106 about a rotation axis 110.

The X-ray source 102 preferably is a controllable X-ray source, such as a tube, for emitting X-rays. Energy is supplied to the X-ray source 102 via a high voltage power supply (not shown). Preferably, during scanning the photon output of the beam is constant. Accordingly, the potential and current supplied to the source are therefore substantially constant during scanning, resulting in an X-ray beam 112 characterized by a substantially constant energy level. Alternatively, the X-ray source can be pulsed so as to provide a pulsed X-ray beam. The output of X-ray source 102 is shaped into the conical beam 112 via a collimator (not shown). The cone shape of the beam 112 preferably has an axis of revolution, defining the axis of transmission of the beam and preferably coaxial with the rotation axis 110. The output of the X-ray source 102 may be monitored with an X-ray level detector (not shown) located proximal to the source to determine the energy level of the emitted X-ray beam 112. The measured energy level may be used in a feedback loop to control the power to the X-ray source, as well as normalize the image data. The X-ray source 102 and detector assembly 106 may be mounted on fixed or rotating frames (not shown) so that the orientation of the source and detector assembly can be rotated relative to a patient on the table 104 about an axis preferably, although not necessarily, parallel to or coplanar with the plane of the table 104. This allows for X-rays images to be generated at any desired angle relative to the patient. An example of a rotating frame is known in the art as a "C" arm.

The radio translucent table 104 is situated within the path of the X-ray beam 112 between the source 102 and detector assembly 106. The X-ray beam 112 propagates through the table 104 with little or no interaction (e.g., attenuation), and the rotatable detector assembly 106, as described, receives the conical X-ray beam 112. A patient (not shown) may be positioned on the top surface 112 of the radio translucent table 104. During operation, the conical beam 112 propagates through the patient. As the beam 112 passes through the patient; the patient attenuates emitted X-ray photons as a function of the density of various tissues in the path of the X-rays. The detector assembly 106 is characterized by a dynamic range and a DQE of the detectors. X-ray photons, within a certain range of energies and not attenuated by the patient, are received and detected by detector assembly 106.

Figure 2:
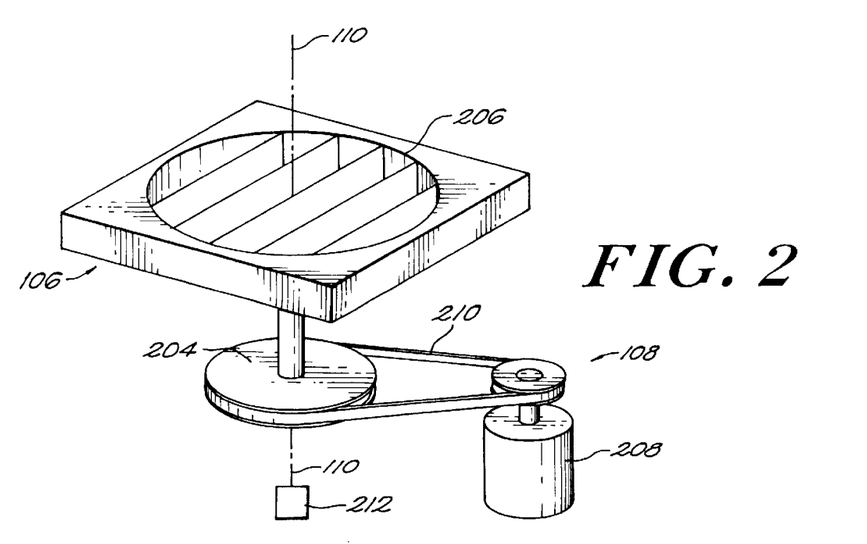
FIG. 2 shows, in perspective, a detailed view of the detector assembly and drive mechanism of the system shown in FIG. 1.

The detector assembly 106 and drive mechanism 108 of this embodiment are shown in more detail in FIGS. 1 and 2. As shown, the detector assembly 106 is rotatably attached to the drive mechanism 108 so as to allow rotation about axis 110. In the preferred embodiment shown, the detector spindle 204 is fixedly attached to the detector assembly 106. The detector assembly 106 includes an input aperture 206 which receives the X-ray radiation emitted by the X-ray source 102. The axis 110 is preferably substantially normal to the plane of the input aperture 206. Thus, the plane of the input aperture 206 is substantially normal to the conical X-ray beam 112. Suitable means such as a drive belt 210 connects a drive mechanism such as motor 208 to the detector spindle 204 so as to translate rotational movement of the drive motor 208 to rotational movement of the detector spindle 204. The angular position of the detector assembly 106 with respect to the frame is measured using, for example, an angular position encoder 212 suitably connected to the spindle 204. The nominal rotational speed of the detector is 120 RPM, although higher and lower speeds may be used depending upon the application. For example, it may be desirable to operate at higher speeds for cardiac applications and lower speeds for orthopedic applications.

Figure 3:
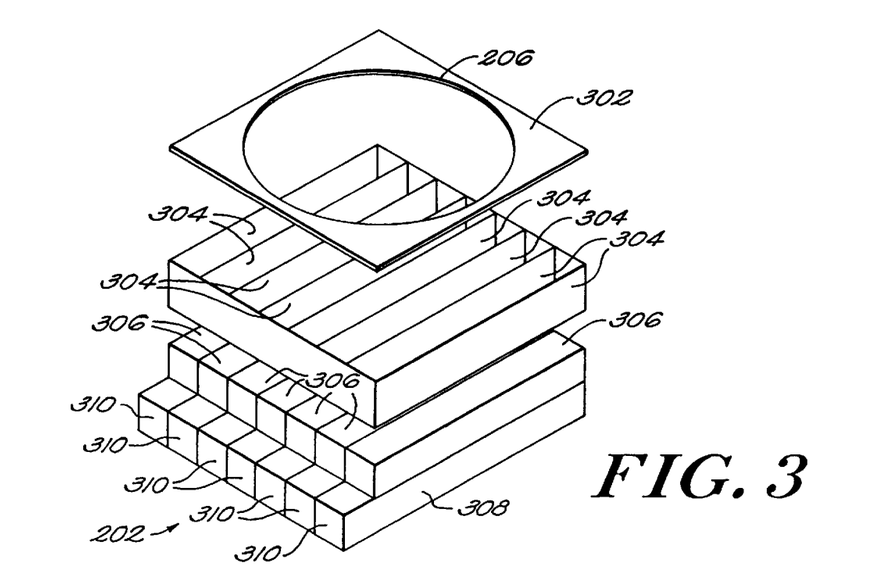
FIG. 3 shows an exploded perspective view of one embodiment of the detector array shown in FIGS. 1 and 2.

As shown in FIG. 3, the preferred detector assembly 106 includes a plurality of layers of elements, all fixedly mounted relative to one another and preferably of equal length and width. In the exemplary configuration of the detector assembly 106 shown in FIG. 3, there are four layers of elements. The top layer includes a mask 302 which defines the aperture 206 of the assembly 106 so as to capture the conical beam. The mask 302 is made of a material, such as lead (Pb) or tantalum (Ta), which presents a high impedance to propagating X-rays. In this embodiment, the aperture 206 of the mask is circular, with the axis 110 preferably passing through the center of the aperture. The aperture is preferably sized so that the diameter of the aperture substantially matches the diameter of the conical X-ray beam 112 where the beam passes through the aperture so that the entire conical beam 112 is always passing through the input aperture 206 during rotation of the assembly during operation of the device. It will be appreciated that other embodiments of the invention may use different input aperture shapes.

In the next layer, the conical X-ray beam 112 is collimated by collimator plates 304 disposed parallel to one another so as to form collimated X-ray fan beam sections. Although for illustrative purposes only seven fan beam sections are shown as being created by the collimator plates in FIG. 3, in any implementation relating to medical imaging, for example, many more collimated fan beams, thinner than shown, are created. The collimator plates are also made of a high impedance material, such as lead (Pb) or tantalum (Ta). The collimator plates 304 are oriented so as to be generally focused on the source of X-ray radiation.

Each fan beam section preferably strikes a corresponding detector of the detector assembly 106. In the embodiment shown the detectors are disposed parallel to one another. Each detector is preferably defined by a scintillator 306, the scintillators 306 being arranged as a 1D array and forming the next layer of the detector assembly 106. Each collimated fan beam section strikes the portion of the corresponding scintillator 306 exposed through the aperture 206 and between the collimator plates 304. Thus, an array of individual scintillators is placed in correspondence with the collimators so that each collimated fan beam section passes between two adjacent collimator plates and irradiates the portion of the corresponding scintillator 306 exposed through the aperture 206. Each scintillator preferably comprises a rectangular parallelepiped of material that converts X-ray photons to optical photons. In a preferred embodiment, the scintillators 306 include cadmium tungstate ($CdWO_4$), although other materials suitable for converting X-ray energy to light energy may be used. The number and density of detectors can vary depending on the application, the ultimate resolution of the image, and limitations relating to cost of the system. In one embodiment of the invention, the number of scintillators is approximately 2000, and the width of each detector (defining the density of the detectors) is approximately 100–200 microns. Thus, the described embodiment requires approximately 2000 scintillators, versus approximately $2000^2$ for a prior art system employing a two dimensional square matrix array of semiconductor detectors, reducing the number of scintillators by 3,998,000. Very clearly, depending upon the application, any number and density of detectors can be utilized, with as little as 100 to 500 (or even less depending on the application), each having a width on the order of 0.5 cm (or even larger depending on the application) still providing relatively good data.

Each of the scintillators 306 is preferably covered on five of its six sides with optically reflective paint. The light generated by a scintillator is thus directed through the only side not covered with reflective paint, which is preferably the surface at the end of each light pipe. This surface is in optical contact with a corresponding transducer 310. The light pipes, which are preferably constructed of bundles of optical fibers, receive and focus the light emitted by the scintillators onto the corresponding transducers 310. Each transducer is a light to electrical-parameter conversion device, i.e., it varies an electrical parameter (e.g., current, voltage, resistance, etc.) at its output as a function of the optical photons it receives from the light pipe. In a preferred embodiment, each transducer includes an optical photo diode, which converts the light it receives to an electrical current, although other light to electrical-parameter conversion devices may be used.

It should be appreciated that the detector assembly can include other types of detection systems including various structures for providing output signals representative of the amount of x-ray flux striking each detector during a measurement interval. For example, the array of scintillators 306, and corresponding light pipes 308 and detectors 310, can be replaced by corresponding semiconductor devices, one for each detector. In addition, materials such as selenium are known for converting x-rays into light and/or electrical signals so that such a material can be used as make the scintillators 306, or alternatively, can be used directly to convert the detected X-rays into an electrical output of each detector so as to eliminate the light pipes and transducers.

The amount and quality of image data collected is, in part, a function of the position of the array of detectors relative to axis 110.

Figure 4:
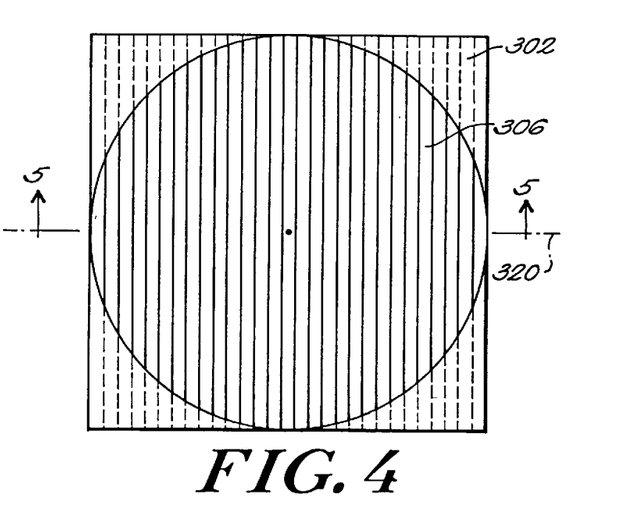
FIG. 4 shows a top view of one embodiment of an arrangement of the detector array which is of the type shown in FIGS. 1–3 illustrating the one-half detector width arrangement.
Figure 5:
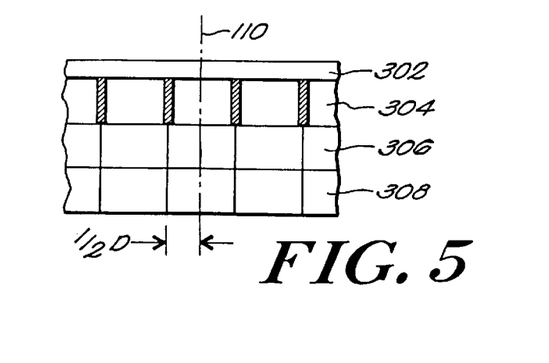
FIG. 5 shows a sectional view, partially cut away, taken along line 5—5 of FIG. 4.

In FIGS. 4 and 5, for example, the detector assembly is positioned so that the axis 110 passes through the center of one of the detectors. A second axis 320 extends normal to the axis 110 and to the longitudinal dimension of the detectors 306 so that the width of each detector can be defined along axis 320. Thus, in this embodiment the transmission axis 110 passes through one of the detectors an equal distance from the two edges defining the width of the intersected detector along axis 320 so as to provide a centered or "one-half" of a detector width arrangement. The detector array need only rotate 180° to provide a complete set of projection data since the data is duplicated with a second 180° rotation.

Figure 6:
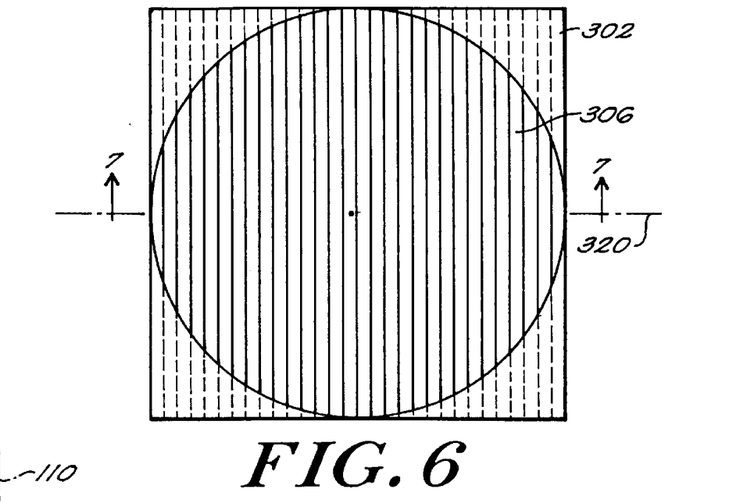
FIG. 6 shows a top view of a second embodiment of an arrangement of the detector array illustrating the one-quarter detector width offset arrangement.
Figure 7:
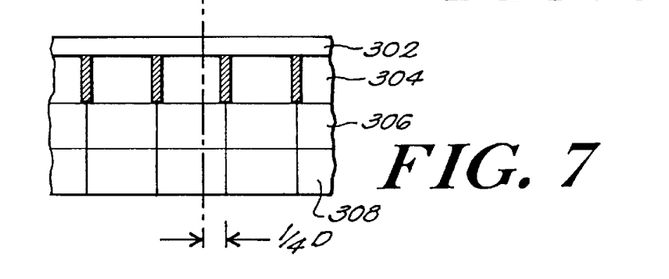
FIG. 7 shows a sectional view, partially cut away, taken along line 7—7 of FIG. 6.

In FIGS. 6 and 7, the amount of data can be essentially doubled by disposing the detectors so that the transmission axis 110 passes through one of the detectors three-quarters from one edge of the detector, and one-quarter from the opposite edge of the detector so as to define a "one-quarter" of a detector width offset along the axis 320 relative to the axis 110. This provides twice the amount of spatial data with one 360° rotation of the detector array than provided with the one-half detector width arrangement, since spatial positioning of the detectors (and thus the image data captured by the detectors) during one 180° part of the 360° rotation is displaced one-half of a detector width from the spatial positioning of the detectors (and thus the image data captured by the detectors) during the other 180° part of the 360° rotation. This projection data acquired during the second 180° of rotation can thus be interleaved with the projection data acquired during the first 180° of rotation. The use of quarter detector offset arrangement reduces image streaks caused by aliasing. When quarter detector offset is used, the center of rotation of the circular mask still coincides with the mechanical center of rotation of the spindle.

Figure 8:
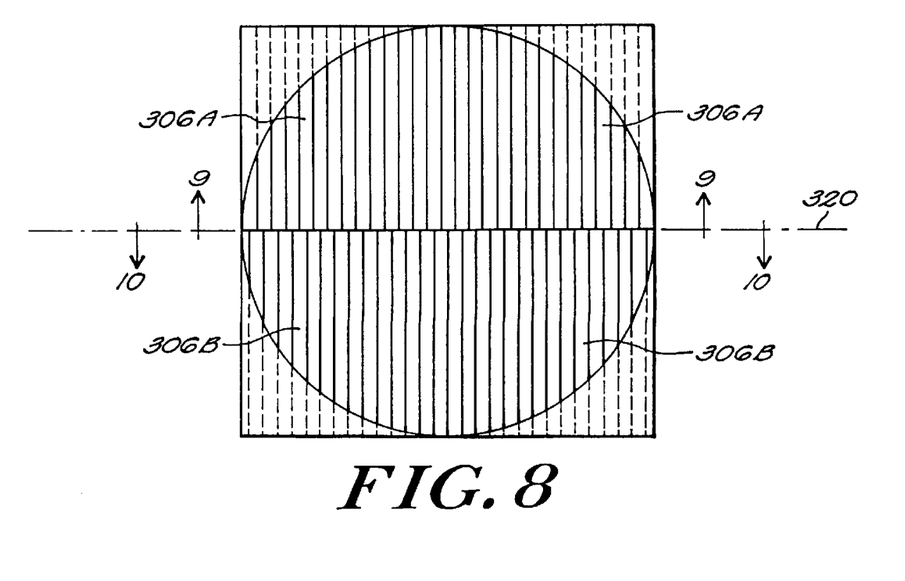
FIG. 8 shows a top view of a third embodiment of an arrangement of the detector array illustrating the one-eighth, tree-eighth detector width offset arrangement.
Figure 9:
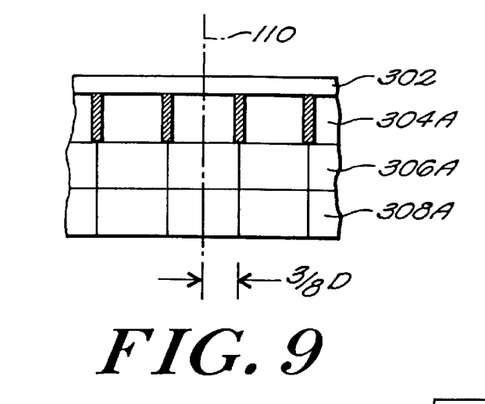
FIG. 9 shows a sectional view, partially cut away, taken along line 9—9 of FIG. 8.
Figure 10:
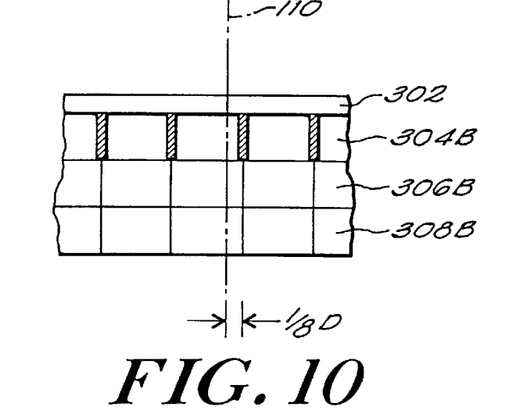
FIG. 10 shows a sectional view, partially cut away, taken along line 10—10 of FIG. 8.

A third possible arrangement is shown in FIGS. 8–10. In this arrangement the detectors can be arranged in a 2D array of two rows. In the embodiment shown each of the detectors for each of the rows includes its own scintillators 306, light pipes 308 and detectors 310, with the letter A being used in the drawings to designate those components for one row, and the letter B being used to designate those components of the other row. The rows are mutually confronting along the axis 320. One row is displaced by "one-quarter" of a detector width offset relative to the other row along the axis 320. However, the transmission axis 110 intersects the axis 320 at a point where one of the detectors of one row is displaced by one-eighth of a detector width offset, while a detector of the other row is displaced by three-eighths of a detector width offset. The spatial positioning (and thus the image data captured by the detectors) of the detectors of one row of the array during one 180° part of the 360° rotation is thus displaced one-quarter of a detector width from the spatial positioning of the detectors of the other row during that portion of the rotation. During the second 180° part of the 360° rotation, the positioning of the spatial data associated with the two rows of detectors are actually shifted one half of a detector width so that the spatial positioning of the associated data is interleaved in four combinations of positions (two from the two rows of detectors during the first 180° rotation, and two from the two rows of detectors during the second 180° rotation) and are displaced or offset by one-quarter of a detector width. Such an arrangement increases the quality of the data from which the image is reconstructed. This arrangement further reduces image streaks caused by aliasing. In this embodiment, the center of rotation of the circular mask still coincides with the mechanical center of rotation of the spindle.

Figure 11:
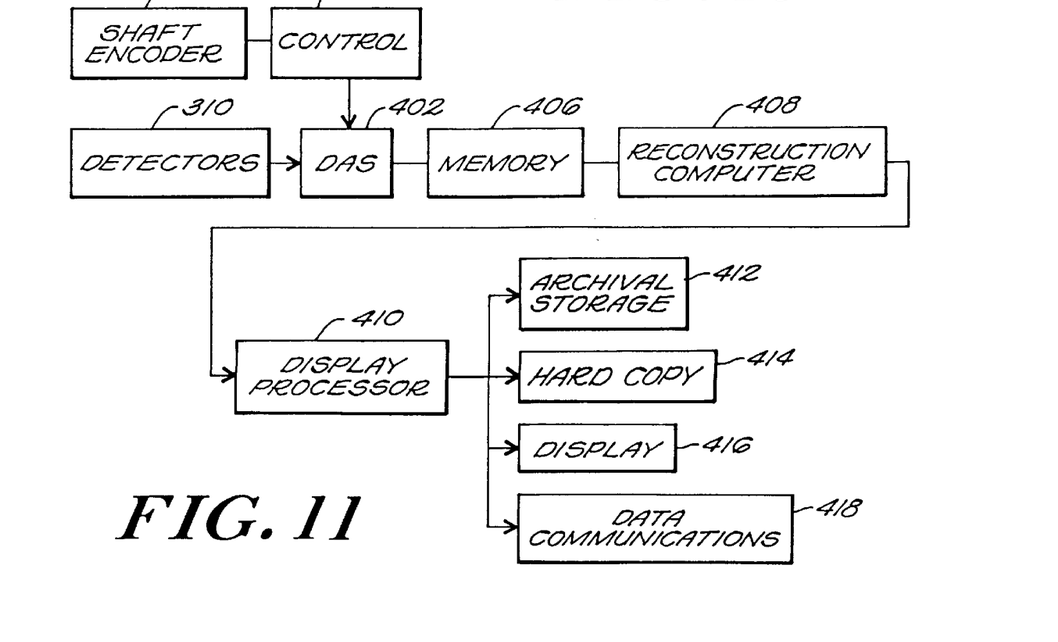
FIG. 11 shows a block diagram of a preferred embodiment of the invention, including the data flow and the processing system for data received from the detectors of the detector assembly.

FIG. 11 shows a block diagram of a preferred embodiment of the system for transmitting and processing the data acquired during the rotation of the detector assembly and for reconstructing an image. As the detector assembly rotates about the axis 110, the shaft encoder 212 provides an indication of the angular position of the assembly about the axis 110 relative to some reference position. The encoder provides an output signal indicating when the detector assembly passes through equal angular increments. At each of these angular positions, the transducers provide a set of outputs to a data acquisition system (DAS) 402. The angular increment between successive readings can be any suitable angle, with 0.25° being typical. An increment of 0.25° provides 720 sets of signals for the 1D array of FIGS. 4 and 5 for a complete 180° rotation, 1440 sets of signals for the 1D array of FIGS. 6 and 7 for a complete 360° rotation, and 1440 sets of signals (with twice as many signals) for the 2D array of FIGS. 8–10 for a complete 360° rotation. Since the detectors are parallel to one another, the data resembles data of parallel projections at precise projection angles, and therefore the data is analogous to parallel projections which are acquired during a CT scan of the third generation type. Each set of signals of a corresponding incremental angle is filtered, amplified and digitized in the DAS 402, which in this embodiment is physically located on the detector assembly 106. A DAS commonly used in commercial CT scanners of the third generation type may be used in the present invention. The drive mechanism 108 thus rotates the detector assembly 106 through the required amount of rotation angle about axis 110 while the patient is exposed to the X-ray radiation. A control unit 404 receives information regarding the angular position of the detector assembly 106 from the angular position encoder 212 and sends command signals to the DAS as a function of the angular position information. At approximately equal incremental angular positions of the detector assembly 106 over the total range of required rotation, the control unit 404 commands the DAS 402 to sample the transducers. At each angular position of the detector assembly 106, the data sampled from the transducers collectively forms a one dimensional projection of the conical projection of the patient. In this embodiment of the invention, the DAS 402 collects approximately 720 projections over the angular range of 180° rotation, or 1440 projections over the angular range of 360° rotation.

The DAS 402 preferably dumps the data into memory 406. This data can be read out and processed by a reconstruction computer 408. The path between the DAS/detector assembly and the memory 406 may include slip rings (not shown) or a wireless local area network (LAN) (not shown) in order to communicate data between the rotating platform and the stationary platform and to supply power and timing information to the DAS. The reconstruction computer 408 preferably cooperates with a display processor 410 for generating an image of the patient using the methods described below, and passes the resulting image data, for example, to archival storage 412, a hard copy maker, display 416, e.g., a CRT, for immediate display, or subsequent transmission by a communications device 418, such as a network adapter, modem, or the like. The CRT can be part of a PACS (not shown).

The reconstruction computer 408 generates an image of the patient by reconstructing the projections using well-known methods developed for commercial CT scanners of the third generation type. The method of filtered back projection (FBP) is preferably used to reconstruct images. FBP includes three principal steps: correction for machine imperfections, filtration, and back projection.

The first step of FBP, correction for machine imperfections, includes the following substeps:

Offset correction: The reconstruction computer 408 measures projection values from the DAS/detector combination in the absence of X-ray radiation. Ideally, these projection values will be zero, but in practical systems finite offsets exist. These offsets are referred to in the art as "dark currents." The reconstruction computer then subtracts "dark currents" offsets from the raw readings from the detectors.

Crosstalk correction: Ideally, each transducer receives light from only its corresponding scintillator. Crosstalk occurs when light meant for a particular transducer "leaks" to one or more of its neighbors. Crosstalk is manifested in the reconstructed images as streaks from high contrast boundaries. The reconstruction computer 408 removes crosstalk by convolving the offset-corrected data with a spatially dependent, finite impulse response (FIR) filter.

Afterglow correction: The scintillators continue to emit light after the X-ray source is turned off; this effect is known as afterglow. The reconstruction computer 408 deconvolves the afterglow using an infinite impulse response (IIR) filter, which can be implemented with a recursive filter.

Beam hardening correction: The X-ray source emits a spectrum of different energy photons. The average energy of the photons that pass unattenuated through the patient increases with path length. This is because in general, the patient's tissues will absorb low energy photons more efficiently than high energy photons, mainly due to photoelectric absorption. This effect, which is known as beam hardening, causes a low frequency shading in reconstructed images. The reconstruction computer 408 removes shading artifacts by adding a correction term to each projection value, where the term is proportional to the magnitude of the projection value. In practice, a fourth-order polynomial can be used to determine the correction terms. The system determines the coefficients of the polynomial by scanning known, uniformly thick and dense objects (e.g., water or homogeneous plastic) and then adjusting the coefficients until the resulting images do not exhibit shading artifacts. The coefficients can also be determined via computer simulation of the spectrum of the X-ray source 102 and any sources of filtration between the X-ray source 102 and the detector assembly 106.

Spectral Correction: The scintillators selectively absorb X-ray photons as a function of the frequency, energy, etc., of the photon. To a first approximation, all the scintillators exhibit the same response and the beam hardening correction can be used to remove the detector's average response. However, each detector usually has a slightly different response to incoming X-rays. These differences are denoted spectral errors, which lead to rings in images. The spectral errors can be removed by scanning objects having uniform thickness and density to detect the rings. The rings can then be subtracted from anatomical images in image space or converted to the projection space and subtracted from projections.

Logarithm: The reconstruction computer 408 determines the logarithm of the projection datum value and the logarithm of the power level of the X-ray source 102, as received by the X-ray level detector. The base of the logarithm is arbitrary, as long as the same base is used for both determinations.

Reference correction: The projections are normalized to the output power level of the X-ray source by subtracting the logarithm of the power level of the X-ray source from the logarithm of the projection data. The reconstruction computer 408 subtracts the appropriate offset value from the level detector value before the logarithmic value is determined.

Air Calibration: During a calibration procedure, the reconstruction computer 408 generates projection data with X-ray radiation but without a patient in the beam. The reconstruction computer corrects the projections per the steps outlined hereinbefore. The reconstruction computer then averages the projections to form what is known as an air correction vector. The projection data of a patient are subtracted from the air correction vector.

The second step of filtered back projection is filtration. The projections are nominally filtered with a kernel whose response is proportional to the magnitude of frequency. In practice, users often desire to trade noise for resolution. Also, users might want to edge-enhance resulting images. Therefore, the nominal filter can include a low-pass filter to reduce noise or a high-pass filter for edge enhancement. The filtration can be performed in the spatial domain or the frequency domain with the use of fast Fourier transforms (FFT).

The last stage of filtered back projection is back projection. This method is well known in the art in connection with third generation CT, and no description is provided. The back projection can be accomplished using dedicated hardware or with a general purpose computer.

In other embodiments, the high voltage supply which provides energy to the X-ray source 102 may alternate between two potentials (voltages). Such an embodiment may be advantageous, for example, when the system is used as a line scanner for scanning items such as luggage or mail. One such dual energy source is described in copending U.S. patent application Ser. No. 08/671,202, entitled "Improved Dual Energy Power Supply," (Attorney Docket No. ANA-094) which is assigned to the same assignee as the present invention and which is incorporated herein in its entirety by reference. Projections at the two potentials can be acquired using an interleaved acquisition technique know in computed tomography. Techniques using dual energy X-ray sources are known for providing additional information about a material's characteristics, beyond solely a density measurement. Techniques using dual energy X-ray sources involve measuring the X-ray absorption characteristics of a material for two different energy levels of X-rays. Depending upon the calibration of the system, dual energy measurements provide an indication of dual parameters of the material being scanned; for example, at one calibration setting, the dual parameters can be chosen to be the material's atomic number and the material's density. At another calibration setting, the dual parameters can be chosen to be the material's Photoelectric coefficients and the material's Compton coefficients. At yet another calibration setting, the dual parameters can be chosen to be an amount of a first material present (e.g., plastic) and an amount of a second material present (e.g., aluminum). Dual energy X-ray techniques for energy-selective reconstruction of X-ray computer tomography images are described, for example, in Robert E. Alvarez and Albert Macovski, "Energy-selective Reconstructions in X-ray Computerized Tomography", *Phys. Med. Biol.* 1976, Vol. 21, No. 5, 733–744; and U.S. Pat. Nos. 4,029,963 and 5,132,998. One algorithm used to generate such dual parameters from dual energy X-ray projection data is known as the Alvarez/Macovski Algorithm. Alternatively, two images can be generated independently for each energy level as described above. In both types of reconstruction, pixel-to-pixel comparisons provide additional discriminants to the clinician.

In practice, the output of the X-ray source is spatially dependent due to the heel effect, in which X-rays are selectively absorbed by the anode, and by spatially dependent intrinsic filtration in the beam. Also in practice, the response to X-rays will not be uniform along the length of each scintillator. The nonuniformity can be caused by scintillator imperfections, collimator mechanical tolerances, light pipe attenuation caused by differing path lengths, and nonuniformity of optical coatings.

Figure 12:
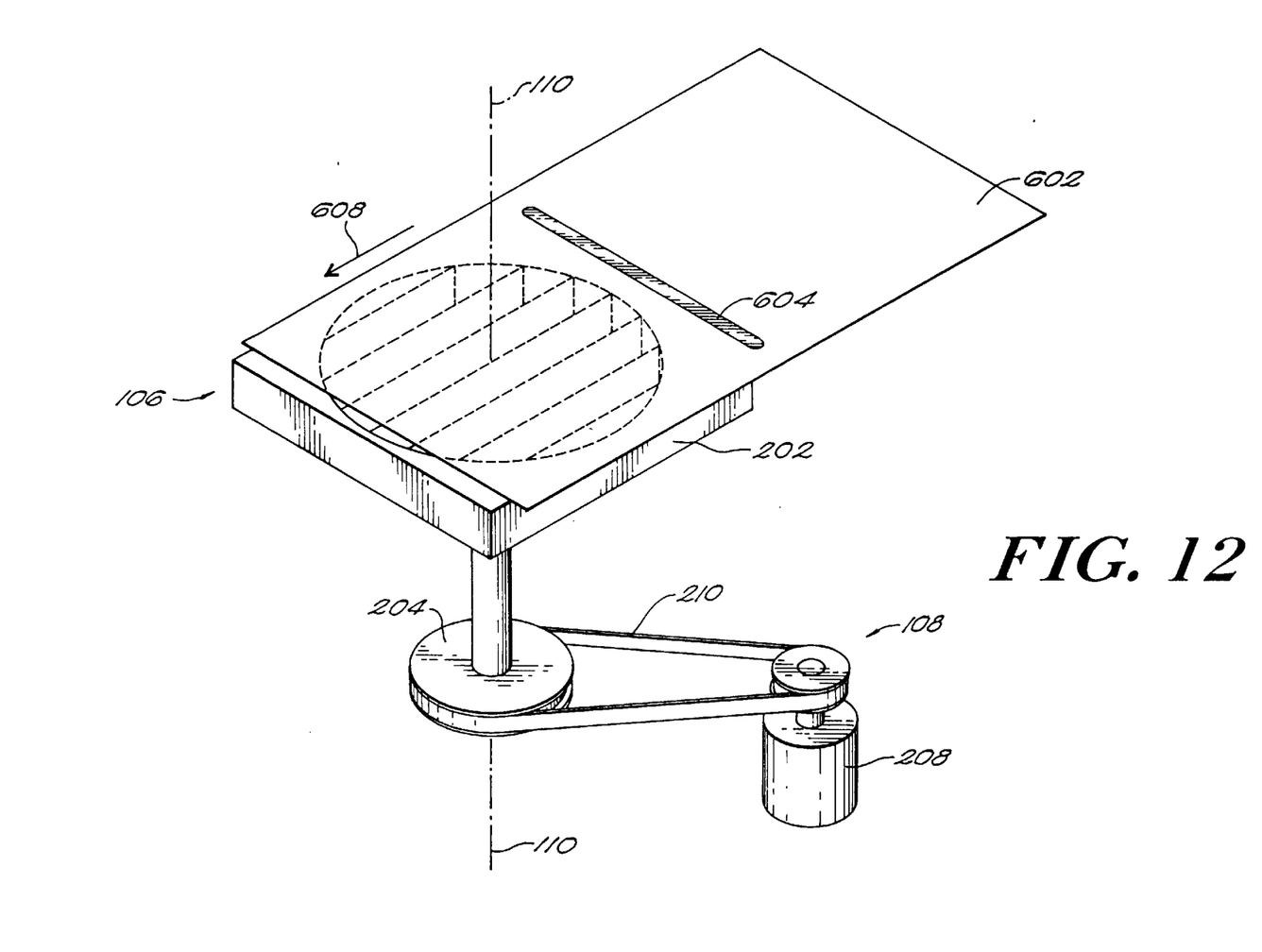
FIG. 12 shows a detailed perspective view of one embodiment of the detector assembly, with a slidable mask for characterizing a collimator/scintillator/detector assembly.
Figure 13:
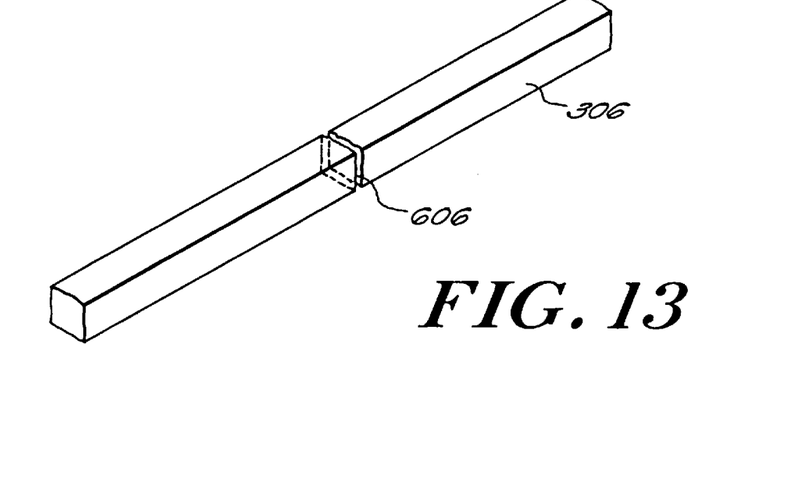
FIG. 13 shows a perspective view of a scintillator of the assembly of FIG. 12 as it is scanned by the slidable mask.

Accordingly, in FIGS. 12 and 13, an alternative embodiment of the invention determines the response of each detector/scintillator/collimator assembly across the scintillator's length by sliding a high impedance (to X-ray radiation) mask 602 with a long, narrow aperture 604 (i.e., a slit) lengthwise in direction 608 past the scintillators with the X-ray source emitting radiation and recording the response each detector produces. The underlying detector array is shown through the mask 602 in FIG. 12 via dashed lines. At any given time during this procedure, only a small "slice" 606 of each scintillator 306 is exposed to X-ray radiation, as illustrated in FIG. 13. The reconstruction computer 408 then incorporates the resulting scintillator response information in the reconstruction algorithms.

In yet another embodiment, the invention compensates for the nonuniform attenuation by using algebraic reconstruction techniques (ART). If the variations in X-ray intensity along the scintillators are low-frequency functions of the scintillator length, the reconstruction computer 408 can modify the filtered back projection to correct the variations; such methods are known in the art as attenuated radon transformations.

In still another embodiment of the invention, the reconstruction computer produces reconstructed images via direct Fourier reconstruction of the corrected data rather than through via filtered back projection.

In another embodiment, the source collimator includes a two dimensional array of plates (not shown), wherein one set of parallel plates are positioned at an angle to a second set of parallel plates so as to form cells, and wherein the cells formed by the intersection of the plates are focused on the X-ray source 102. The collimator can also be replaced by the anti-scatter device used in conventional film systems called a grid. Furthermore, it is possible to operate the system without any collimation.

Other X-ray detectors that can be used include sodium iodine, high-pressure xenon gas, gadolinium oxysulfate, or rare earth doped ceramics. The scintillators, light pipes and transducers can be replaced with devices which include materials that convert X-ray photons directly to electric current. An example of such a material is cadmium telluride and selenium.

The detector offsets (dark currents) can be a function of the temperatures of the detectors and the DAS. In still another embodiment of the invention, one or more temperature sensing devices may be placed on or near the DAS/detector assemblies to sense the temperature of these assemblies at the time data are acquired. A base offset table, which can be updated infrequently, can be adjusted to the present operating temperature using, for example, a three-term Taylor series expansion. The coefficients of the expansion can be determined during a calibration procedure in which the detector and DAS are cycled through their normal operating temperature range using external heat control devices (not shown).

The afterglow effects are also a function of the temperature of the detector. Another embodiment of the invention may incorporate temperature sensors at or near the detectors and series expansions to adjust the afterglow correction to the present operating temperature of the detector, similar to the method used to correct for temperature dependence of the dark currents.

The air data are also a function of the temperatures of the detectors. Yet another embodiment of the invention may incorporate temperature sensors on or near the detectors and series expansions to adjust the air data to the present operating temperature of the detector, similar to the method used to correct for the temperature dependence of the dark currents and the afterglow effects.

Further embodiments of the invention may include corrections to mitigate other system imperfections. For example, the detrimental effects of patient motion may be mitigated by applying weighting coefficients or nonlinear filters to the projection data in either projection space or image space. Streaks in images caused by aliasing can be reduced or eliminated by applying nonlinear filters to the data. Artifacts caused by timing errors in the angular position of the spindle with respect to the DAS timing can be corrected by interpolating projections to their correct angular position. To produce uniform images, the scintillators must be evenly spaced with known centers; if the centers are not correct, the data can be compensated via linear interpolation to account for the shift if the actual positions are known. Some X-ray tubes generate secondary radiation called off-focal radiation near the apex of the conical beam; the effect of this off-focal radiation can be reduced by convolving the projections with a spatially dependent, FIR filter.

When all the corrections noted above are applied, residual rings can still be present in reconstructed images. These rings can be reduced by detecting lines in the projection data or by detecting rings in images. Methods known to those skilled in the art can be used for the detection of the rings and lines, and for subsequent use of the information for ring reduction.

Figure 14:
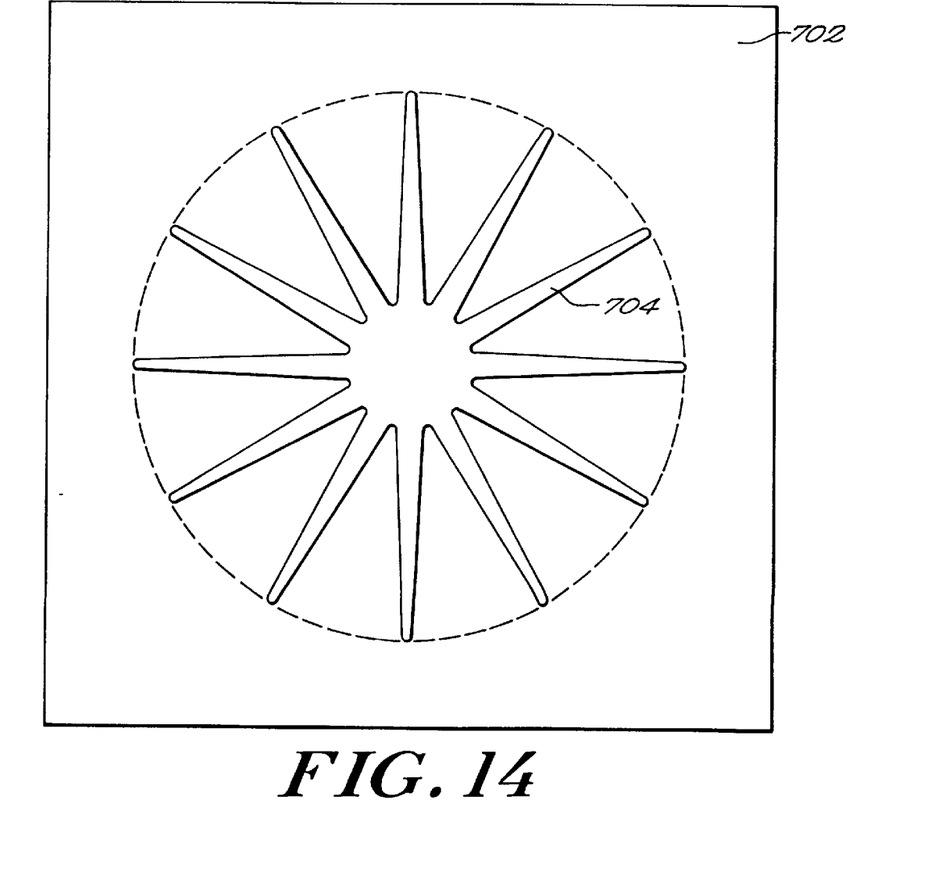
FIG. 14 shows a top view of an embodiment of one detector mask having a star shaped input aperture pattern.

In yet another embodiment of the invention, the mask 302 shown in FIG. 3 having a circular input aperture 206 may be replaced with a mask 702 having a star shaped input aperture 704 as shown in FIG. 14. The use of the circular input aperture 206 leads to images that have lower noise at their periphery, but also with lower resolution. The use of star mask increases the noise and the resolution at the periphery, and reduces the total number of projections which must be acquired (relative to a circular mask) in order to attain similar results. In the illustrated embodiment, the star aperture has 12 "arms", although the number, size and shape of the star arms may be varied to produce different image characteristics.

The X-ray source 102 can also include an assembly (not shown) to collimate the conical X-ray radiation source to a fan beam. In such an embodiment of the invention, the fan-beam is positioned perpendicular to the length of the scintillators. Additionally, a rectangular mask (not shown) can be positioned over the detector to coincide with the fan beam. In this configuration, the system can be converted and used as a conventional CT scanner. More specifically, the detector and X-ray source 102 can be rotated about the longitudinal axis of the patient. In this configuration, the detector is not rotated on its spindle. Furthermore, the patient can be translated relative to the fan beam to acquire helical CT data or planar images with an axial extent larger than the diameter of the detector.

In another embodiment of the invention, the transducers can be placed at other positions along the light pipes, and the light pipes take other forms. For example, the light pipes could be shaped as fans with the apex connected to transducers. The light pipes and scintillators could be split into two or more sections to allow multiple slice CT scanning.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of generating digital X-ray images, said method comprising the steps of:
   defining a beam of X-ray radiation propagating along a first axis;
   defining and configuring a plurality of detectors along a second axis substantially normal to said first axis;
   rotating said detectors about said first axis and in a plane substantially normal to said first axis so as to generate digital projection image data; and
   generating an image from the digital projection image data using computed tomography reconstruction techniques.

2. A method according to claim 1, wherein each of said plurality of detectors receives said X-ray radiation and converts said X-ray radiation to a signal corresponding to at least one characteristic of said radiation.

3. A method according to claim 2, said signal being a sequence of voltage transitions.

4. A method according to claim 2, wherein said characteristic of said radiation includes one of the following: energy level, frequency and amplitude.

5. A method according to claim 2, wherein each of said plurality of detectors includes a transducer which receives said X-ray radiation and produces an output signal as a function of said characteristic.

6. A method according to claim 5, wherein said transducer includes semiconductor material.

7. A method according to claim 6, wherein the semiconductive material is cadmium telluride.

8. A method according to claim 2, wherein each of said plurality of detectors includes:
   a scintillating material which receives said X-ray radiation and produces a variable light output as a function of said characteristic; and,
   a device which receives said variable light output and produces an output signal as a function of said characteristic.

9. A method according to claim 8, wherein said scintillating material includes one of the following: cadmium tungstate (CdWO$_4$), selenium, sodium iodine, high-pressure xenon, gadolinium oxysulfate and rare earth doped ceramics.

10. A method according to claim 8, wherein said variable light output of said scintillating material is spatially dependent, further comprising calibration steps of:
    removing objects from said X-ray beam, so as to provide a clear path from an X-ray source to said detectors;
    sliding a mask along said scintillating material in a direction substantially parallel to said second axis, said mask including a material which provides a relatively high impedance to X-ray propagation, said mask further including an aperture so as to pass said radiation to said scintillating material within a spatially restricted region;
    recording said output signal as a function of said mask position along said scintillating material; and
    modifying said digital projection image data as a function of said recorded output signal so as to compensate for said spatial dependence of said scintillating material.

11. A method according to claim 2, wherein each of said plurality of detectors includes selenium.

12. A method according to claim 2, wherein each of said plurality of detectors includes a collimator for confining a first portion of said beam to said detector and excluding other portions of said beam.

13. A method according to claim 2, wherein said plurality of detectors includes a mask having an input aperture for selectively passing said radiation to said detectors.

14. A method according to claim 13, wherein said input aperture is substantially circular.

15. A method according to claim 13, wherein said input aperture is substantially star-shaped.

16. A method according to claim 13, wherein said mask includes a shielding material which provides a relatively high impedance to X-ray propagation.

17. A method according to claim 16, wherein said shielding material includes one of the following: lead (Pb) and tantalum (Ta).

18. A method according to claim 1, further including:
    sampling said detectors at substantially equal incremental angular positions over a range of rotation, so as to produce a plurality of projection data sets, each of which represents X-ray radiation received by said detectors at a corresponding one of said angular positions; and
    reconstructing said projection data sets so as to produce an image representative of the portion of an object through which said X-ray radiation passes.

19. A method according to claim 18, wherein said range of rotation is substantially equal to 180 degrees.

20. A method according to claim 18, wherein said range of rotation is substantially equal to 360 degrees.

21. A method according to claim 18, wherein said step of reconstructing said projection data includes back filtered projection reconstruction techniques.

22. A method according to claim 18, wherein said step of reconstructing said projection data includes algebraic reconstruction techniques.

23. A method according to claim 18, wherein said step of reconstructing said projection data includes direct Fourier reconstruction techniques.

24. A method according to claim 18, further including the step of correcting each of said projection data sets for at least one of a plurality of system imperfections, said system imperfections including: dark current offsets, transducer crosstalk, scintillating material afterglow, beam hardening, detector spectral response variations, and X-ray beam level variations.

25. A method according to claim 24, wherein at least one of said system imperfections is temperature dependent, and said step of correcting further includes:

sensing an average temperature of said plurality of detectors; and including said sensed averaged temperature in said correction of said projection data sets.

26. A method according to claim 18, wherein said beam of X-ray radiation alternates between a first energy level and a second energy level.

27. A method according to claim 18, wherein each of said plurality of detectors is defined by a width along said second axis, and one of the detectors intersects said first axis so as to divide said width of the intersected detector into two substantially equal lengths.

28. A method according to claim 18, wherein each of said plurality of detectors is defined by a width along said second axis, and one of the detectors intersects said first axis so as to divide the width into a first length and a second length, said first length being approximately one quarter of said width of the intersected detector and said second length being approximately three quarters of said width of the intersected detector.

29. A method according to claim 28, wherein said range of rotation is substantially equal to 360 degrees, and said projection data sets taken from a rotation range of zero degrees to 180 degrees are interleaved with projection data sets taken from a rotation range of 180 degrees to 360 degrees.

30. A method according to claim 18, wherein said plurality of detectors are arranged in two rows, each of said plurality of detectors is defined by a width along said second axis, and one of the detectors of the first row intersects said first axis so as to divide the width into a first length and a second length, said first length being approximately one eighth of said width of the intersecting detector of said first row and said second length being approximately seven eighths of said width of the intersecting detector of said first row, and one of the detectors of the second row intersects said first axis so as to divide the width into a first length and a second length, said first length being approximately three eighths of said width of the intersecting detector of said second row and said second length being approximately five eighths of said width of the intersecting detector of said second row.

31. A method according to claim 30, wherein said range of rotation is substantially equal to 360 degrees, and said projection data sets taken from a rotation range of zero degrees to 180 degrees are interleaved with projection data sets taken from a rotation range of 180 degrees to 360 degrees.

32. An x-ray imaging system for generating digital projection images, said system comprising:

a source of X-ray radiation constructed and arranged so as to define a beam of X-ray radiation along a first axis;

a plurality of detectors, disposed along a second axis substantially normal to said first axis;

a rotation mechanism constructed and arranged so as to rotate the detectors about said first axis and in a plane substantially normal to said first axis so as to generate digital projection image data and an image reconstruction subsystem constructed and arranged so as to generate a computed tomographic image as a function of the digital projection image data.

33. A system according to claim 32, wherein each of said plurality of detectors receives said X-ray radiation and converts said X-ray radiation to a signal corresponding to at least one characteristic of said radiation.

34. A system according to claim 33, said signal being a sequence of voltage transitions.

35. A system according to claim 33, wherein said characteristic of said radiation includes one of the following: energy level, frequency and amplitude.

36. A system according to claim 33, wherein each of said plurality of detectors includes a transducer which receives said X-ray radiation and produces an output signal as a function of said characteristic.

37. A system according to claim 36, wherein said transducer includes cadmium telluride.

38. A system according to claim 33, wherein each of said plurality of detectors includes selenium.

39. A system according to claim 33, wherein each of said plurality of detectors includes:

a scintillating material which receives said X-ray radiation and produces a variable light output as a function of said characteristic; and, a converter which receives said variable light output and produces an output signal as a function of said characteristic.

40. A system according to claim 39, wherein said scintillating material includes one of the following: cadmium tungstate ($CdWO_4$), selenium, sodium iodine, high-pressure xenon, gadolinium oxysulfate and rare earth doped ceramics.

41. A system according to claim 39, wherein said variable light output of said scintillating material is spatially dependent, further comprising:

a mask, mounted so as to be slidable relative to said plurality of detectors in a direction substantially parallel to said second axis after all objects have been removed from said beam between said source and said mask, said mask including material which provides a high impedance path to X-ray radiation, said mask further including an aperture so as to pass said radiation to said scintillating material within a spatially restricted region;

storage memory constructed and arranged so as to store said output signal as a function of said mask position along said scintillating material; and a reconstruction computer constructed and arranged so as to reconstruct said projection image data so as to produce an image representative of the portion of an object through which said X-ray radiation passes, and which modifies said projection image data as a function of said recorded output signal so as to compensate for said spatial dependence of said scintillating material.

42. A system according to claim 32, wherein each of said plurality of detectors includes a collimator for confining a first portion of said beam to said detector and excluding other portions of said beam.

43. A system according to claim 32, wherein said plurality of detectors includes a mask having an input aperture constructed and arranged so as to selectively pass said radiation to said detectors.

44. A system according to claim 43, wherein said input aperture is substantially circular.

45. A system according to claim 43, wherein said input aperture is substantially star-shaped.

46. A system according to claim 43, wherein said mask includes a shielding material which provides a relatively high impedance to X-ray propagation.

47. A system according to claim 46, wherein said shielding material includes one of the following: lead (Pb) and tantalum (Ta).

48. A system according to claim 32, further including:

a data acquisition system constructed and arranged so as to acquire data from said detectors at substantially equal angular increments over a range of rotation, so as to produce a plurality of projection data sets, each of which is a function of the X-ray radiation received by said detectors at a corresponding one of said angular increments; and a reconstruction computer constructed and arranged so as to reconstruct an image of the portion of the object as a function of the plurality of projection data sets.

49. A system according to claim 48, wherein said range of rotation is substantially equal to 180 degrees.

50. A system according to claim 48, wherein said range of rotation is substantially equal to 360 degrees.

51. A system according to claim 48, wherein said reconstruction computer includes an image reconstruction subsystem constructed and arranged so as to reconstruct an image using back filtered projection reconstruction techniques.

52. A system according to claim 48, wherein said reconstruction computer includes an image reconstruction subsystem constructed and arranged so as to reconstruct an image using algebraic reconstruction techniques.

53. A system according to claim 48, wherein said reconstruction computer includes an image reconstruction subsystem constructed and arranged so as to reconstruct an image using direct Fourier reconstruction techniques.

54. A system according to claim 48, further including a correction system which corrects each of said projection data sets for at least one of a plurality of system imperfections, said system imperfections including: dark current offsets, transducer crosstalk, scintillating material afterglow, beam hardening, detector spectral response variations, and X-ray beam level variations.

55. A system according to claim 54, wherein at least one of said system imperfections is temperature dependent, and said correction system further includes:

a temperature sensing device which senses an average temperature of said plurality of detectors; and a temperature compensation section of said reconstruction computer which varies said correction of said projection data sets as a function of said average temperature.

56. A system according to claim 54, wherein said beam of X-ray radiation alternates between a first energy level and a second energy level.

57. A system according to claim 32, wherein each of said plurality of detectors is defined by a width along said second axis, and one of the detectors intersects said first axis so as to divide said width of said intersected detector into two substantially equal lengths.

58. A system according to claim 32, wherein each of said plurality of detectors is defined by a width along said second axis, and one of the detectors intersects said first axis so as to divide said width of the intersected detector into a first length and a second length, said first length being approximately one quarter of said width and said second length being approximately three quarters of said width.

59. A system according to claim 58, wherein said range of rotation is substantially equal to 360 degrees, and said projection data sets taken from a rotation range of zero degrees to 180 degrees are interleaved with projection data sets taken from a rotation range of 180 degrees to 360 degrees.

60. A system according to claim 32, wherein said plurality of detectors are arranged in two rows, each of said plurality of detectors is defined by a width along said second axis, and one of the detectors of the first row intersects said first axis so as to divide the width into a first length and a second length, said first length being approximately one eighth of said width of the intersecting detector of said first row and said second length being approximately seven eighths of said width of the intersecting detector of said first row, and one of the detectors of the second row intersects said first axis so as to divide the width into a first length and a second length, said first length being approximately three eighths of said width of the intersecting detector of said second row and said second length being approximately five eighths of said width of the intersecting detector of said second row.

61. A system according to claim 60, wherein said range of rotation is substantially equal to 360 degrees, and said projection data sets taken from a rotation range of zero degrees to 180 degrees are interleaved with projection data sets taken from a rotation range of 180 degrees to 360 degrees.

62. A system according to claim 32, wherein said rotating means includes:

a motor having a housing, and an armature rotatably attached to said housing, said housing being disposed in a stationary position with respect to said X-ray source;

a spindle fixedly attached to said plurality of detectors; and, a belt mechanically coupling said spindle and said armature, so as to translate rotational motion of said armature to rotational motion of said spindle.

63. A system according to claim 32, further including a sensing arrangement constructed and arranged so as to sense the angular position of the plurality of detectors about said first axis, and generate said digital projection image data at equal angular increments.

64. A method according to claim 32, wherein the image reconstruction subsystem is constructed and arranged so as to generate a computed tomographic image as a function of the digital projection image data using back filtered projection reconstruction techniques.

65. A method according to claim 32, wherein the image reconstruction subsystem is constructed and arranged so as to generate a computed tomographic image as a function of the digital projection image data using algebraic reconstruction techniques.

66. A method according to claim 32, wherein the image reconstruction subsystem is constructed and arranged so as to generate a computed tomographic image as a function of the digital projection image data using direct Fourier reconstruction techniques.

* * * * *